US012733986B2

(12) United States Patent
Altmann et al.

(10) Patent No.: US 12,733,986 B2
(45) Date of Patent: Sep. 15, 2026

(54) DIRECTING AN ULTRASOUND PROBE USING KNOWN POSITIONS OF ANATOMICAL STRUCTURES

(71) Applicant: Biosense Webster (Israel) Ltd., Yokneam (IL)

(72) Inventors: Andres Claudio Altmann, Haifa (IL); Assaf Govari, Haifa (IL); Ido Ilan, Yokneam (IL); Morris Ziv-Ari, Atlit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 236 days.

(21) Appl. No.: 17/555,836

(22) Filed: Dec. 20, 2021

(65) Prior Publication Data

US 2023/0190382 A1 Jun. 22, 2023

(51) Int. Cl.

| | |
|---|---|
| ***A61B 34/20*** | (2016.01) |
| ***A61B 8/00*** | (2006.01) |
| ***A61B 8/08*** | (2006.01) |
| ***A61B 8/12*** | (2006.01) |

(52) U.S. Cl.

CPC ............ *A61B 34/20* (2016.02); *A61B 8/0841* (2013.01); *A61B 8/085* (2013.01); *A61B 8/0883* (2013.01); *A61B 8/12* (2013.01); *A61B 8/463* (2013.01); *A61B 8/4488* (2013.01); *A61B 2034/2063* (2016.02)

(58) Field of Classification Search

CPC ....... A61B 34/20; A61B 8/0841; A61B 8/085; A61B 8/0883; A61B 8/12; A61B 8/463; A61B 8/4488; A61B 2034/2063

See application file for complete search history.

(56) References Cited

U.S. PATENT DOCUMENTS

| | | | |
|---|---|---|---|
| 6,332,089 | B1 | 12/2001 | Acker et al. |
| 6,618,612 | B1 | 9/2003 | Acker et al. |
| 6,711,429 | B1 | 3/2004 | Gilboa et al. |
| 7,604,601 | B2 | 10/2009 | Altmann et al. |
| 7,974,681 | B2 | 7/2011 | Wallace et al. |
| 10,918,310 | B2 | 2/2021 | Cohen et al. |
| 2002/0065455 | A1 | 5/2002 | Ben-Haim et al. |
| 2003/0120150 | A1 | 6/2003 | Govari |
| 2004/0068178 | A1 | 4/2004 | Govari |

(Continued)

FOREIGN PATENT DOCUMENTS

| | | |
|---|---|---|
| JP | 2006-521150 A | 9/2006 |
| JP | 2006-305357 A | 11/2006 |

(Continued)

OTHER PUBLICATIONS

International Search Report mailed Feb. 6, 2023 from corresponding PCT application PCT/IB2022/060766.

*Primary Examiner* — Amal Aly Farag

(74) *Attorney, Agent, or Firm* — Smith, Gambrell & Russell LLP

(57) ABSTRACT

A method includes manipulating a catheter, which includes an ultrasound transducer array, inside an organ of a patient so as to acquire ultrasound images of at least part of the organ. One or more reference positions are identified of one or more respective reference anatomical structures in or near the organ. The ultrasound images are annotated with annotations indicating the identified reference anatomical structures.

20 Claims, 4 Drawing Sheets

(56) References Cited

U.S. PATENT DOCUMENTS

| | | | | |
|---|---|---|---|---|
| 2006/0253031 | A1 | 11/2006 | Altmann et al. | |
| 2007/0032826 | A1* | 2/2007 | Schwartz | A61B 34/20 607/2 |
| 2007/0106146 | A1 | 5/2007 | Altmann et al. | |
| 2007/0223794 | A1 | 9/2007 | Preiss et al. | |
| 2007/0276226 | A1 | 11/2007 | Tal | |
| 2008/0300487 | A1* | 12/2008 | Govari | A61B 8/0883 600/443 |
| 2009/0177089 | A1 | 7/2009 | Govari et al. | |
| 2012/0165671 | A1* | 6/2012 | Hill | A61B 8/14 600/443 |
| 2012/0174022 | A1* | 7/2012 | Sandhu | G16H 40/63 715/781 |
| 2019/0021699 | A1 | 1/2019 | Bracken et al. | |
| 2020/0146579 | A1* | 5/2020 | Bar-Tal | A61B 5/341 |
| 2021/0015453 | A1 | 1/2021 | Toporek et al. | |
| 2021/0065882 | A1* | 3/2021 | McLeod | G06T 7/187 |

FOREIGN PATENT DOCUMENTS

| | | | |
|---|---|---|---|
| JP | 2007-117746 | A | 5/2007 |
| JP | 2007-268259 | A | 10/2007 |
| JP | 2019-501728 | A | 1/2019 |
| WO | 1996005768 | A1 | 2/1996 |
| WO | 2020/084039 | A1 | 4/2020 |

* cited by examiner

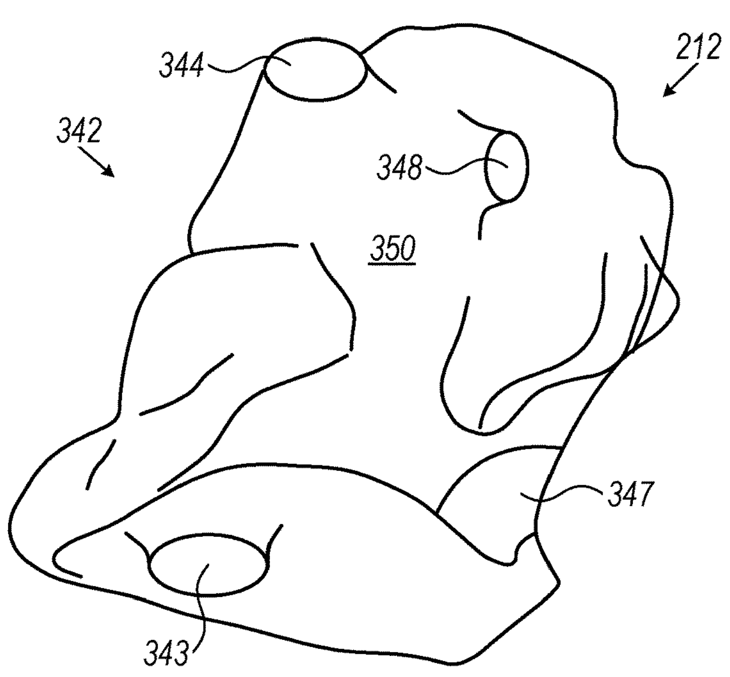
FIG. 4
FIG. 5
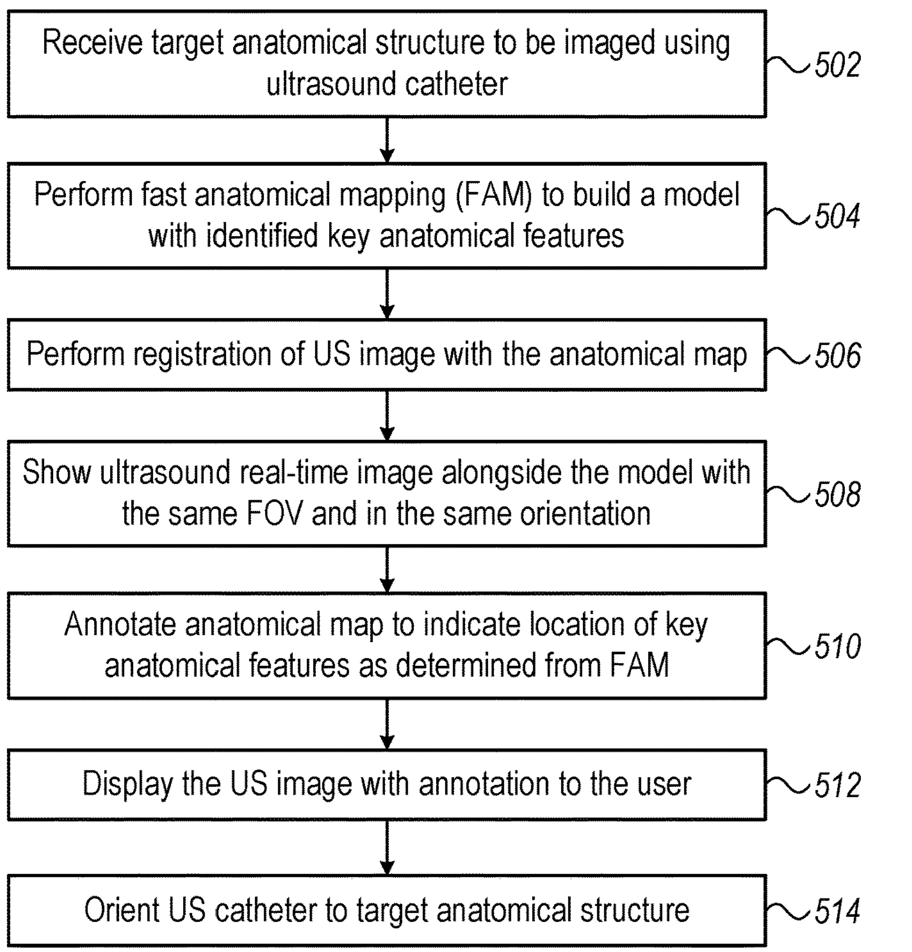

DIRECTING AN ULTRASOUND PROBE USING KNOWN POSITIONS OF ANATOMICAL STRUCTURES

FIELD OF THE INVENTION

The present invention relates generally to intra-body medical probes, and particularly to imaging of anatomical structures using medical ultrasound (US) probes.

BACKGROUND OF THE INVENTION

In practice, it is often difficult for physicians conducting procedures using ultrasound to understand the orientation of the field of view (FOV) of an ultrasound probe in relation to the anatomy of the organ. This problem may exist for 2D image slices as well as for 3D images (in the case of 4D US). A physician may not intuit how best to adjust the position and rotation of the probe in space to view the region of interest (ROI).

Various methods for imaging organs using medical ultrasound probes have been proposed. For example, U.S. Pat. No. 7,604,601 describes a medical imaging system for imaging a patient's body, including a catheter having a position sensor and an ultrasonic imaging sensor. The position sensor transmits electrical signals indicative of positional information of a portion of the catheter in a patient's body and the ultrasonic imaging sensor transmits ultrasonic energy at a target in the patient's body, receives ultrasonic echoes reflected from the target in the patient's body and transmits signals relating to the ultrasonic echoes reflected from the target in the patient's body. A positioning processor is operatively connected to the catheter for determining positional information of the portion of the catheter based on the electrical signals transmitted by the position sensor. The system also includes a display and an image processor operatively connected to the catheter, the positioning processor and the display. The image processor displays on the display a catheter icon in a same orientation as an orientation of the portion of the catheter in the patient's body based on positional information derived from the position sensor. The image processor also generates an ultrasonic image of the target based on the signals transmitted by the ultrasonic sensor and depicts in real-time the generated ultrasound image on a display in a same orientation as the orientation of the portion of the catheter in the patient's body based on positional information derived from the position sensor.

As another example, U.S. Pat. No. 6,711,429 describes a system and method of displaying at least one point-of-interest of a body during an intra-body medical procedure. The method is effected by (a) establishing a location of the body; (b) establishing a location of an imaging instrument being for imaging at least a portion of the body; (c) defining at least one projection plane being in relation to a projection plane of the imaging instrument; (d) acquiring at least one point-of-interest of the body; and (e) projection said at least one point-of-interest on said at least one projection plane; such that, in course of the procedure, the locations of the body and the imaging instrument are known, thereby the at least one point-of-interest is projectable on the at least one projection plane even in cases whereby a relative location of the body and the imaging instrument are changed.

However, there remains a need for faster, more intuitive, and accurate modes for guiding and/or automating the process of imaging a ROI within the body.

SUMMARY OF THE INVENTION

An embodiment of the present invention that is described hereinafter provides a method including manipulating a catheter, which includes an ultrasound transducer array, inside an organ of a patient so as to acquire ultrasound images of at least part of the organ. One or more reference positions are identified of one or more respective reference anatomical structures in or near the organ. The ultrasound images are annotated with annotations indicating the identified reference anatomical structures.

In some embodiments, identifying the reference positions includes recording multiple catheter positions, at which the catheter is positioned while imaging the multiple reference anatomical structures, respectively.

In some embodiments, recording the catheter positions includes measuring the catheter position by a position tracking system.

In an embodiment, annotating the ultrasound images includes annotating an anatomical map, which is displayed registered with an ultrasound image, and using the annotations on the anatomical map to annotate the ultrasound image.

In another embodiment, the anatomical map is acquired during a same invasive procedure in which the ultrasound image is acquired.

In some embodiments, annotating the ultrasound images includes annotating, in real-time, an ultrasound image acquired by the catheter.

In some embodiments, the method further includes using the annotations, re-positioning the catheter to image a target anatomical structure of the organ.

In other embodiments, re-positioning the catheter includes calculating a target position of the catheter relative to a geometrical model of the organ, the model specifying relative positions of the reference anatomical structures and the target anatomical structure.

In an embodiment, re-positioning the catheter includes estimating a relative location and a relative orientation of the catheter with respect to the target anatomical structure based on known relative locations and relative orientations between the reference anatomical structures and the target anatomical structure.

In another embodiment, re-positioning the ultrasound catheter includes at least one of displacing the catheter and rotating the catheter.

In some embodiments, wherein the organ is a heart.

In some embodiments, the method further includes predicting landmark locations using the one or more reference positions and a generally known anatomy of the organ.

In some embodiments, predicting landmark locations includes generating and presenting an abstract labeling map comprising labels put at relative known and predicted locations of anatomical structures of the organ.

There is additionally provided, in accordance with another embodiment of the present invention, a system including a catheter and a processor. The catheter, which includes an ultrasound transducer array, is configured to be manipulated inside an organ of a patient so as to acquire ultrasound images of at least part of the organ. The processor is configured to (i) identify one or more reference positions of one or more respective reference anatomical structures in or near the organ, and (ii) annotate the ultrasound images with annotations indicating the identified reference anatomical structures.

It is noted that the methods and systems disclosed herein may be employed for use with 2D or 4D ultrasound systems. The term "4D ultrasound catheter" refers to a catheter incorporating a 2D array of ultrasound transducers. The term "4D ultrasound image" refers to a time-series of 3D ultrasound images of a certain volume acquired by the 2D array.

A 4D image can be regarded as a 3D movie, the fourth dimension being time. Another way of describing 4D image (or rendering) is as a time-dependent 3D image (or rendering). Where used in the heart, a 4D ultrasound catheter may be referred to as "4D Intracardiac Echocardiography (ICE)" catheter.

The present invention will be more fully understood from the following detailed description of the embodiments thereof, taken together with the drawings in which:

BRIEF DESCRIPTION OF THE DRAWINGS

FIG. 4 is a schematic, pictorial illustration of an anatomical map used in annotating reference anatomical structures on an ultrasound image acquired in real time by the system of FIG. 1, in accordance with an embodiment of the present invention; and FIG. 5 is a flow chart that schematically describes a second method of directing an ultrasound fan using a known position of anatomical structures, in accordance with an embodiment of the present invention.

DETAILED DESCRIPTION OF EMBODIMENTS

Overview

Embodiments of the present invention that are described herein provide methods and systems that use a probe, such as a catheter, with an array of ultrasound transducers for producing ultrasound images of a selected target anatomical structure.

In the disclosed embodiments, a processor, or a user, uses known locations of and/or orientations to anatomical structures encountered by the catheter, or structures imaged by the catheter and/or identified on an anatomical map, to estimate a location and/or orientation into which a physician (or robot) needs to manipulate the catheter's ultrasound array in order to image the selected target anatomical structure.

Figure 3:
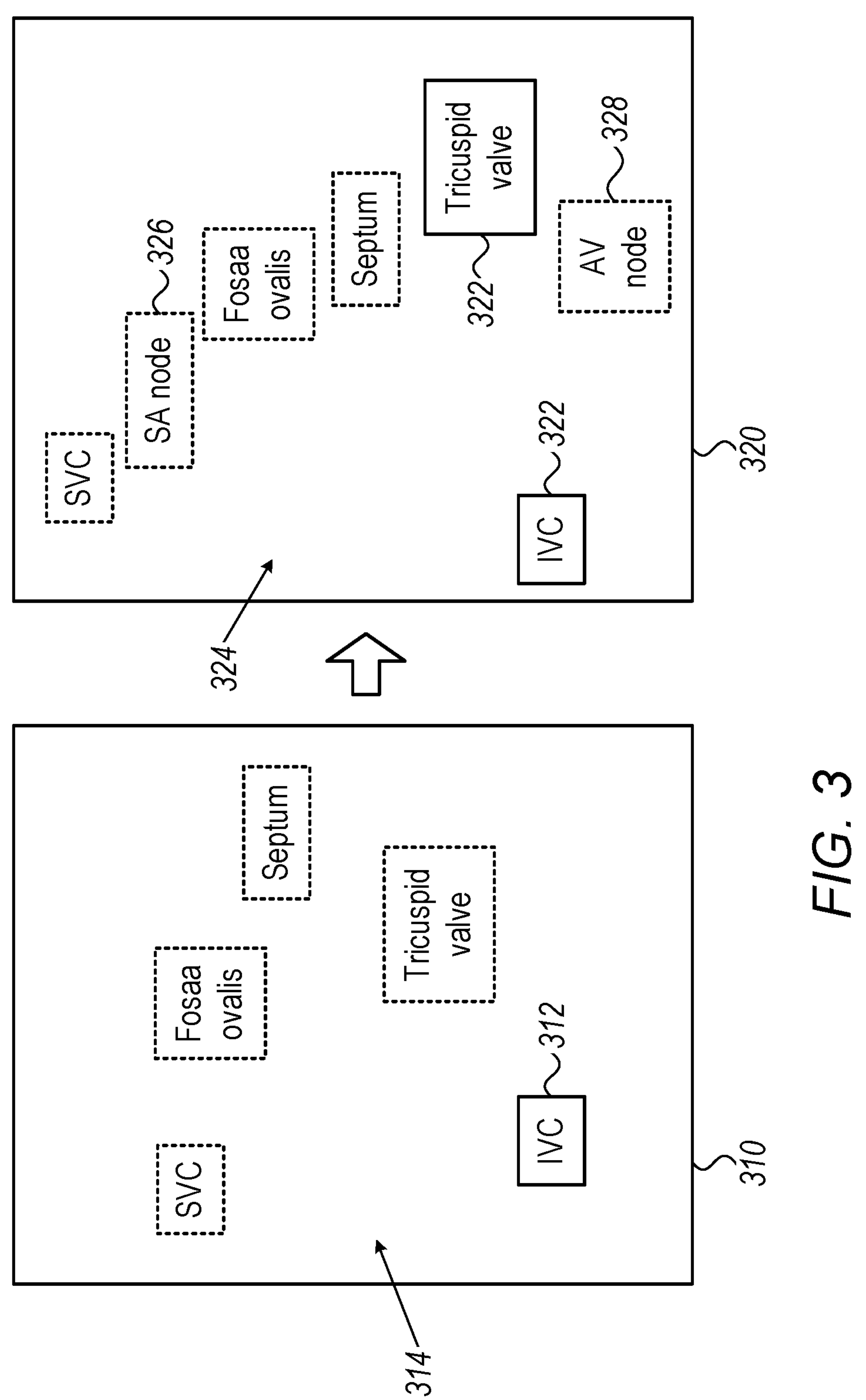
FIG. 3 is a schematic, pictorial illustration of an automatically updated abstract labeling map of the right atrium seen in FIG. 1, the labeling map used in predicting locations of anatomical landmarks, in accordance with an embodiment of the present invention.

Still, the information encountered by the catheter is partial (incomplete) and in one example, the disclosed technique lets a user to complete it on-the-fly based on prediction. The predication is based on the general anatomy of the heart being known. As the user advances/moves the catheter the user identifies some anatomical structures and then can infer location of additional anatomical structures based on the ones that the user identified. This process is manifested, for example, in a form of an automatically updated abstract labeling map given to a user performing an ultrasound scan of an organ, with labels of known and of predicted locations of anatomical features of the organ. In this map, the labels arranged according to expected relative locations of the actual anatomical landmarks, and the predicted relative locations become progressively more accurate with the advancement of the ultrasound catheter. Thus, every imaging step that show an actual anatomy of the organ assists a physician performing the imaging to navigate the ultrasound catheter to such predicted locations, as shown in FIG. 3.

In doing so, the disclosed technique relies on the general anatomy of the heart (or other relevant anatomy) being known and being similar for different patients, including the relative spatial arrangement of various anatomical structures. Additionally or alternatively, an anatomical model of the relevant anatomy should be available, such as a fast anatomical model (FAM) being generated such that the relative spatial arrangements of the of anatomical landmarks of the anatomy (e.g., the heart) are known by reference to the model. Therefore, once the catheter's position (i.e., location and orientation) is known relative to the coordinate system of the heart, it is possible to move and/or orient the catheter to image any target anatomy. Orienting the probe may be manual, or automated with robotic control.

To this end, a processor annotates the real-time acquired ultrasound image with reference (e.g., landmark) anatomical features. Based on the annotation, the ultrasound probe may be manually or automatically oriented to any desired anatomical structure. Two example methods disclosed below can be used to achieve the annotation. Either one or both together may be used. Combining both methods (completely or parts thereof) may provide improved results, e.g., higher accuracy. Typically, the processor displays the annotations on the real-time US image.

In some embodiments, the first method comprises the steps of:

1. Progressively collecting information regarding location of landmark anatomical features as the catheter probe moves through the body to the organ of interest. The landmarks may be marked by the physician and/or automatically detected. Example cardiac-relevant landmarks include chest bones, superior vena cava, inferior vena cava, tricuspid valve.
2. Concurrently collecting information regarding movement of probe in 3D space.
3. Optionally using predication to locate additional landmarks based collect information. The predication may be an automated process.
4. Annotating the real time US images with the landmarks detected.
5. Determining orientation of the catheter within the organ based the location of landmark anatomical features on the US image and the known movement path of the catheter.
6. Optionally, orienting the catheter to desired structure, e.g., fossa ovalis. Orienting may be automated with robotic control. Optionally, orienting may be semi-automated based on receiving instructions on how to move the catheter. Orienting may be manual based on displaying annotated real-time US image.

For example, assuming that a cardiac physician operating an ultrasound catheter with a one-dimensional (1D) or two-dimensional (2D) ultrasound array wants to image the fossa ovalis (typically before performing a transeptal puncture). The physician inserts the catheter through the inferior vena cava (IVC). When the catheter is in the IVC, the physician identifies the IVC and marks its location and/or orientation. If the catheter has electrodes, and an ACL (advanced current location) tracking system is implemented, the identification may be automatic.

The physician then advances the catheter until it images another structure, in this example the superior vena cava (SVC). This is also noted by the physician, so that the location and/or orientation of the SVC with respect to the catheter are known. In one embodiment, the physician records the SVC as having, for example, a reference orientation.

When the locations and/or orientations of IVC and SVC are noted (e.g., as coordinates recorded by the processor, tagged on a visual user interface, or on a map), the position and/or orientation of the catheter within the heart is now known (with respect to the IVC and the SVC) so that there is now sufficient information for the ultrasound beam of the catheter to be positioned and/or oriented so it can image any desired anatomical structure, assumed to be, by way of example, the fossa ovalis. (The catheter may be oriented automatically or manually.)

The above description assumes that just two heart structures (the IVC and the SVC) are used to translate and/or orient the catheter. If these two structures are insufficient (e.g., they are not well defined or there are relatively large errors in their location and/or orientation) any other easily identified structure, for example, inside the right atrium, may be used, e.g., the tricuspid valve.

The system described here may be used for imaging other cardiac structures, for example, specific pulmonary veins, the left atrium appendage, and the left or right ventricles.

In some embodiments, the second method comprises the steps of:

1. Performing anatomical mapping (in some embodiments, fast anatomical mapping (FAM) (e.g., by acquiring a small number of data-points/contours) to build a model of at least part of the heart with identified key anatomical features. The FAM is typically performed on a same session as the one at which the US images are acquired, as described below.
2. Performing registration to relate coordinates of image pixels in US image (or voxels in case of a 3D/4D US image) to coordinates of the anatomical map.
3. Showing an ultrasound real-time image alongside the model, so that the anatomical model is displayed with the same FOV and in the same orientation as the real time US image.
4. Annotating the anatomical map, the real time image, or both, to indicate the locations of key anatomical features as determined from FAM, and display the US image with the annotation to the user.
5. Optionally, orienting the catheter to desired structure, e.g., fossa ovalis.

In some embodiments, the US catheter also comprises an integral position sensor, such as a magnetic position sensor, that is preregistered with the ultrasound array. The array produces a fan or sector-shaped ultrasound beam, and is thus able to image an anatomical structure of an organ, such as of a cardiac chamber. Because of the integral position sensor, the spatial coordinates (e.g., location and/or orientation) of the catheter and of voxels of the anatomical structure are known. In such embodiments, a processor receives catheter locations and/or orientations from a tracking system using the sensor. The processor singles out coordinates when anatomical structures are visualized by the ultrasound array, so as to generate the reference location and/or orientation required in order for a user to bring (e.g., displace or orient) the catheter in position to image the target anatomical structure, e.g., one required by the physician to be imaged.

In some embodiments, an ultrasound imaging method is provided, that includes (a) manipulating a catheter, which comprises an ultrasound transducer array, inside an organ of a patient so as to image multiple reference anatomical structures of the organ, (b) recording multiple catheter positions, at which the catheter is positioned while imaging the multiple reference anatomical structures, respectively, and (c) re-positioning the catheter to image a target anatomical structure of the organ based on (i) identities of the reference anatomical structures and (ii) the respective recorded catheter positions while imaging the reference anatomical structures.

In an embodiment, re-positioning the catheter includes calculating a target position of the catheter relative to a geometrical model of the organ, the model specifying relative positions of the reference anatomical structures and the target anatomical structure. For example, the geometrical model is of at least apportion of the heart.

System Description

Figure 1:
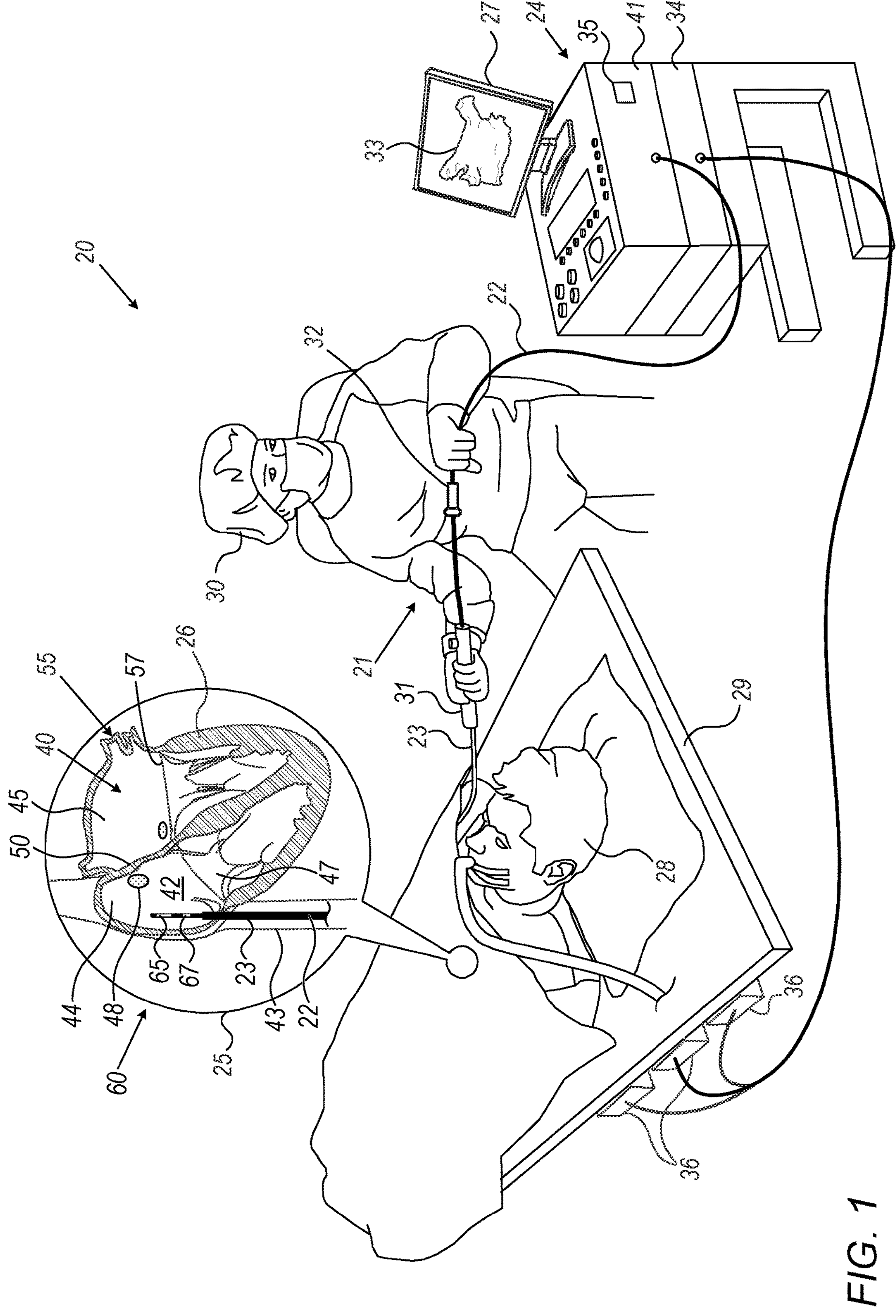
FIG. 1 is a schematic, pictorial illustration of a catheter-based ultrasound imaging system using a catheter with a distal end assembly comprising an ultrasound array and a position sensor, in accordance with an embodiment of the present invention.

FIG. 1 is a schematic, pictorial illustration of a catheter-based ultrasound imaging system 20 using a catheter 21 with a distal end assembly 60 (shown in an inset 25) comprising an ultrasound array 65 and a position sensor 67, in accordance with an embodiment of the present invention. Ultrasound-array 65 can be 1D or 2D in order to generate 2D or 3D ultrasound images, respectively. Integral position sensor 67 is preregistered with array 65 of catheter 21.

Specifically, sensor 67 is configured to output signals indicative of a location and orientation of the ultrasound transducer array 65 inside the organ. A processor of the system is configured to use the sensor's signal output to acquire one or more ultrasound images of anatomical structures oriented in various respective orientations relative to ultrasound transducer array 65.

As seen, distal end assembly 60 is fitted at the distal end of a shaft 22 of the catheter. Shaft 22 is inserted through a sheath 23 into a heart 26 of a patient 28 lying on a surgical table 29. The proximal end of shaft 22 is connected to a control console 24.

A physician 30 navigates distal end assembly 60 of catheter 21 via the inferior vena cava (IVC) 43 to image the fossa ovalis 48 (typically before performing a transeptal puncture). When in IVC 43 the IVC is identified by the physician. If the catheter has electrodes, and an ACL (advanced current location) system is implemented, the identification may be automatic.

As shown in inset 25, distal end assembly 60 is then advanced inside right atrium 42 until array 65 images another structure, assumed herein to be superior vena cava (SVC) 44. This is noted by the physician so that the orientation of SVC 44 with respect to the catheter is known. When the orientation is noted, the location and orientation of the catheter within the heart is now known (with respect to SVC 44 and the IVC 43) so that there is now sufficient information for the ultrasound fan of the catheter to be oriented to any desired structure, assumed here to be towards fossa ovalis 48. (The catheter may be oriented automatically or manually.)

To this end, in one embodiment the user or the processor tags identified structures and performs necessary calculations of orientations, so that processor can recommend where, and in which orientation, to place the catheter. Based on processor recommendations, or by user digression using a known orientation, the processor or the user can place a fan icon at the suggested location and orientation.

To rotate the ultrasound array into a required orientation, the physician can, for example, use a manipulator 32 near the proximal end of the catheter.

The above description assumes that only two heart structures (the IVC and the SVC) are used to orient the catheter. If these two structures are insufficient (e.g., they are not well defined or there are relatively large errors in their orientation) any other easily identified structure may be used, e.g., tricuspid valve 47 or other reference (e.g., landmark) anatomical features of right atrium 42.

The system described here may be used for imaging other structures, for example, septum wall 50 between atria, specific pulmonary veins 55 and left atrium 45, left atrium appendage 57, and the left or right ventricles.

Control console 24 comprises a processor 41, typically a general-purpose computer, with suitable front end and interface circuits 38 for receiving signals from catheter 21. Console 24 also comprises a driver circuit 34 configured to drive magnetic field generators 36. During the navigation of distal end 22 in heart 26, console 24 receives location and orientation signals from position sensor 52 in response to magnetic fields from external field generators 36. Magnetic field generators 36 are placed at known positions external to patient 28, e.g., below table 29 upon which the patient is lying. These location and orientation signals are indicative of the location and orientation of ultrasound-array 65 in a coordinate system of the position tracking system.

The method of location and orientation sensing using external magnetic fields is implemented in various medical applications, for example, in the CARTO™ system, produced by Biosense Webster, and is described in detail in U.S. Pat. Nos. 6,618,612 and 6,332,089, in PCT Patent Publication WO 96/05768, and in U.S. Patent Application Publications 2002/0065455, 2003/0120150, and 2004/0068178, whose disclosures are all incorporated herein by reference.

An imaged target anatomical structure (e.g., portion of right atrium 42, or of left atrium 45, such as pulmonary vein 55 ostium) is presented to physician 30 by processor 41 on a monitor 27, e.g., as a volume rendering 33.

In the embodiment described herein, catheter 21 is used for ultrasound-based diagnostic purposes, although the catheter may be further used to perform electrical sensing and/or ablation of tissue in heart 26, using, for example, one or more electrodes (not shown) disposed on the distal end.

Processor 41 is programmed in software to carry out the functions described herein. The software may be downloaded to a memory 35 of the computer in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, including in FIG. 2, that enables processor 41 to perform the disclosed steps, as further described below.

The example configuration shown in FIG. 1 is chosen purely for the sake of conceptual clarity. The disclosed techniques may similarly be applied using catheter access other than through IVC 43, such as another vein or via an artery.

Figure 2:
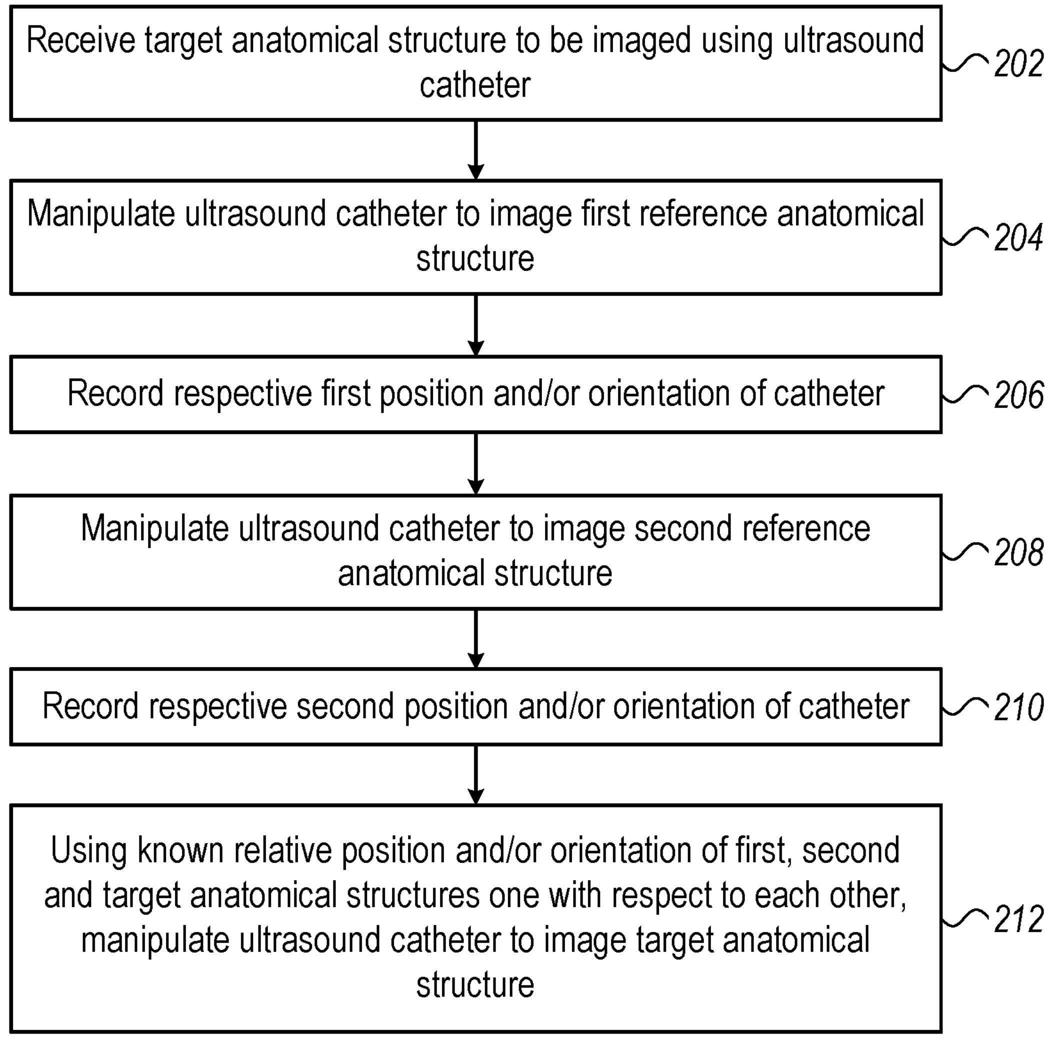
FIG. 2 is a flow chart that schematically describes a first method of directing an ultrasound fan using a known position of anatomical structures, in accordance with an embodiment of the present invention.

A First Method of Directing an Ultrasound Fan Using Known Positions of Anatomical Structures FIG. 2 is a flow chart that schematically describes a method of directing an ultrasound fan (e.g., as generated by array 65 of FIG. 1) using known positions of anatomical structures, in accordance with an embodiment of the present invention. The algorithm, according to the presented embodiment, carries out a process that begins with processor 41 receiving (e.g., from physician 30) a target anatomical structure to be imaged using catheter 21, at a target imaging receiving step 202.

Next, the physician manipulates ultrasound catheter 21 so array 65 can image a first reference anatomical structure (e.g., IVC 43), at a first imaging step 204.

The processor, or the user, records respective first coordinates of catheter, which can be location and/or orientation of the array, at a first recording step 206.

The physician then manipulates (e.g., distally advances) ultrasound catheter 21 so array 65 can image a second reference anatomical structure (e.g., SVC 44), at a second imaging step 208.

The processor, or the user, records respective second coordinates of the catheter, which can be a location and/or orientation of the array, at a second recording step 210.

Finally, at an imaging step 212, using the recorded coordinates, the physician manipulates the ultrasound catheter so that array 65 can image the target anatomical structure (e.g., superior fossa 48).

The example flow chart shown in FIG. 2 is chosen purely for the sake of conceptual clarity. For example, additional steps, such as imaging a third reference anatomical structure, may be performed.

FIG. 3 is a schematic, pictorial illustration of an automatically updated abstract labeling map 310 of the right atrium 42 seen in FIG. 1, the labeling map used in predicting locations of anatomical landmarks based on already mapped location and general anatomy, in accordance with an embodiment of the present invention. In initial labeling map 310, label 312 indicate a known location of the IVC entrée into right atrium 42, i.e., one observed with the ultrasound probes. Based on label 312 and the generally known heart anatomy, processor 28 adds to map 310 labels 314 of predicted landmark relative locations of SVC 44, fossa ovalis 48, and tricuspid valve 47.

As the ultrasound catheter images the tricuspid valve, this landmark becomes known. Based on labels 322 and the generally known heart anatomy, processor 28 adjust the relative locations of labels 314 into more accurate relative locations of respective labels 324 on an updated labeling map 320. Furthermore, processor 28 adds to map 320 labels 326 of predicted landmark locations of Sinus node (SA node), shown by a label 326, and of Atrioventricular Node (AV node) shown by a label 328.

A Second Method of Directing an Ultrasound Fan Using Known Positions of Anatomical Structures As noted above, the second method involves performing fast anatomical mapping (FAM) to build a model of at least part of the heart with identified key anatomical features. Using the model, the US beam is directed in real-time towards a target anatomical structure with known relation to reference anatomical structures the user or the processor annotate on the map.

FIG. 4 is a schematic, pictorial illustration of an anatomical map 342 used in annotating reference anatomical structures on an ultrasound image acquired in real time by system 20 of FIG. 1, in accordance with an embodiment of the present invention. Typically, anatomical map is acquired by inserting an additional, mapping catheter (not shown), such as a multi-electrode catheter (e.g., the multi-arm Pentaray® catheter or the Lasso® catheter, both catheters made by Biosense Webster.). Performing FAM using these catheters is described, for example, in U.S. Pat. No. 10,918,310, whose disclosure is incorporated herein by reference.

FIG. 4 shows schematically an anatomical map of the right atrium 42 seen in FIG. 1. The mapped right atrium schematics 342 shows landmarks that appear in FIG. 1. For example, anatomical map 342 shows inferior vena cava (IVC) ostium schematics 343, superior vena cava (SVC) ostium schematics 344, tricuspid valve schematics 347, fossa ovalis schematics 348, and inter-atria septum schematics 350.

Annotating anatomical map 342, to indicate location of at least some of the above key anatomical features 343, 344, 347, 348 and 350, as determined from FAM is a step in the aforementioned second method for directing an ultrasound catheter towards another anatomical feature.

Map 342 is brought by way of example and simplified on purpose to maintain clarity of presentation. Actual maps may, for example, include more map layers, such as of electrical activity of cardiac tissue, and/or an ultrasound image registered with the map.

FIG. 5 is a flow chart that schematically describes a second method of directing an ultrasound fan (e.g., as generated by array 65 of FIG. 1) using a known position of anatomical structures, in accordance with an embodiment of the present invention. The algorithm, according to the presented embodiment, carries out a process that begins with processor 41 receiving (typically from physician 30) a target anatomical structure to be imaged using catheter 21, at a target imaging receiving step 502.

Next, using a mapping catheter, system 20 performs FAM to build a model map with identified key anatomical features, such as map 342, at a model FAM mapping step 504. Alternatively, system 20 may perform the FAM using an US catheter similar to catheter 21 but with one or more electrodes disposed over its distal end.

At a registration step 506, processor 41 of system 20 registers a US image acquired by catheter 21 with the anatomical map.

At a presentation step 508, processor 41 shows an ultrasound real-time image alongside the model. Typically, the anatomical model is displayed with the same FOV and in the same orientation as the real time image. For example, if the real-time image displayed is a slice, then the same slice view of the model will be displayed alongside of the real-time image.

At an annotation step 510, physician 30 or processor 41 annotate the anatomical map, the real time image, or both, to indicate location of key anatomical features as determined from FAM.

At a displaying step 512, processor 41 displays the US image with the annotation to the user.

Finally, at an US catheter reorientation step 514, using the annotations, physician 30 (or a robotic system) orients the catheter to a desired (i.e., target) anatomical structure. One exemplary robotic system capable of orienting catheter is described by U.S. Pat. No. 7,974,681, whose disclosure is incorporated herein.

Although the embodiments described herein mainly address the cardiac ultrasound imaging with a catheter, the technique described herein can also be used in imaging other organs, such as of the gastro system.

It will thus be appreciated that the embodiments described above are cited by way of example, and that the present invention is not limited to what has been particularly shown and described herein above. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:

receiving, in real-time, via a display, at least one ultrasound image of at least part of an organ of a patient acquired by an ultrasound transducer array of a first catheter inserted into the patient;

acquiring, using a second catheter configured to be inserted into the patient, intracardiac electrocardiogram signals and location information;

building, using the intracardiac electrocardiogram signals and location information, an anatomical map representing measured locations of one or more reference anatomical structures in or near the organ, by identifying one or more reference positions of the one or more respective reference anatomical structures;

generating, via a processor, an abstract labeling map that predicts locations, within the organ, of additional anatomical structures that are not represented in the anatomical map, the predicted locations being determined based on the identified one or more reference positions and a generally known anatomical model of the organ;

registering and overlaying, via the processor, the abstract labeling map with the at least one received ultrasound image in real-time;

annotating, via the processor, the at least one received ultrasound image and the anatomical map with annotations indicating the identified reference anatomical structures;

re-positioning, using the annotations, at least one of the first catheter and the second catheter to image a target anatomical structure of the organ; and displaying, via the display, the annotated anatomical map with the at least one annotated ultrasound image.

2. The method according to claim 1, wherein identifying the reference positions comprises recording multiple catheter positions of the at least one of the first catheter and the second catheter, at which the at least one of the first catheter and the second catheter is positioned while imaging the multiple reference anatomical structures, respectively.

3. The method according to claim 2, wherein the recording the multiple catheter positions of the at least one of the first catheter and the second catheter comprises measuring the multiple catheter positions by a position tracking system.

4. The method according to claim 1, wherein the anatomical map is acquired during a same invasive procedure in which the ultrasound image is acquired.

5. The method according to claim 1, wherein re-positioning the at least one of the first catheter and the second catheter comprises calculating a target position of the at least one of the first catheter and the second catheter relative to a geometrical model of the organ, the model specifying relative positions of the reference anatomical structures and the target anatomical structure.

6. The method according to claim 1, wherein re-positioning the catheter comprises estimating a relative location and a relative orientation of the catheter with respect to the target anatomical structure based on known relative locations and relative orientations between the reference anatomical structures and the target anatomical structure.

7. The method according to claim 1, wherein re-positioning the ultrasound catheter comprises at least one of displacing the catheter and rotating the catheter.

8. The method according to claim 1, wherein the organ is a heart.

9. The method according to claim 1, further comprising predicting landmark locations using the one or more reference positions and a generally known anatomy of the organ.

10. The method according to claim 9, wherein predicting landmark locations comprises generating and presenting an abstract labeling map comprising labels put at relative known and predicted locations of anatomical structures of the organ.

11. A medical imaging system, comprising:

a processor, which is configured to:

receive, in real-time, via a display, at least one ultrasound image of at least a part of an organ of a patient acquired by an ultrasound catheter within or near the organ in-vivo;

acquire, using a second catheter configured to be inserted into the patient, intracardiac electrocardiogram signals and location information;

build, using the intracardiac electrocardiogram signals and location information, an anatomical map representing measured locations of one or more reference anatomical structures in or near the organ, by identifying one or more reference positions of the one or more respective reference anatomical structures;

generate, based on the one or more reference positions and a generally known anatomical model of the organ, an abstract labeling map that predicts positions, within the organ, of additional anatomical structures that are not represented in the anatomical map;

register and overlay, in real-time and via a processor, the abstract labeling map with the at least one received ultrasound image;

annotate, via the processor, the at least one received ultrasound image and the anatomical map with annotations indicating the identified reference anatomical structures;

automatically determine an orientation adjustment of the ultrasound catheter to obtain an image of a target anatomical structure based on the predicted positions of the additional anatomical structures in the abstract labeling map; and display, via the display, the annotated anatomical map with the at least one annotated ultrasound image.

12. The system according to claim 11, wherein the processor is configured to identify the reference positions by recording multiple catheter positions of the at least one of the first catheter and the second catheter, at which the at least one of the first catheter and the second catheter is positioned while imaging the multiple reference anatomical structures, respectively.

13. The system according to claim 12, wherein the processor is configured to record the multiple catheter positions of the at least one of the first catheter and the second catheter by measuring the multiple catheter positions by a position tracking system.

14. The system according to claim 11, wherein the anatomical map is acquired during a same invasive procedure in which the ultrasound image is acquired.

15. The system according to claim 11, wherein the processor is configured to recommend re-positioning the at least one of the first catheter and the second catheter by calculating a target position of the at least one of the first catheter and the second catheter relative to a geometrical model of the organ, the model specifying relative positions of the reference anatomical structures and the target anatomical structure.

16. The system according to claim 11, wherein the processor is configured to recommend re-positioning the catheter by estimating a relative location and a relative orientation of the catheter with respect to the target anatomical structure based on known relative locations and relative orientations between the reference anatomical structures and the target anatomical structure.

17. The system according to claim 11, wherein the processor is configured to recommend at least one of displacing the catheter and rotating the catheter.

18. The system according to claim 11, wherein the organ is a heart.

19. The system according to claim 11, wherein the processor is further configured to predict relative location of additional landmark locations using the one or more reference positions and a generally known anatomy of the organ.

20. The system according to claim 19, wherein the processor is configured to predict landmark locations by generating and presenting an abstract labeling map comprising labels put at relative known and predicted locations of anatomical structures of the organ.

* * * * *